United States Patent [19]
Janssens et al.

[11] Patent Number: 5,932,569
[45] Date of Patent: Aug. 3, 1999

[54] TRIAZOLOBENZAZEPINE DERIVATIVES

[75] Inventors: Frans Eduard Janssens, Bonheiden, Belgium; Jean Fernand Armand Lacrampe, Le Mesnil-Esnard; Isabelle Noelle Constance Pilatte, Louviers, both of France

[73] Assignee: Janssen Pharmaceutica, N.V., Beerse, Belgium

[21] Appl. No.: 08/433,388

[22] PCT Filed: Nov. 25, 1993

[86] PCT No.: PCT/EP93/03320

§ 371 Date: May 8, 1995

§ 102(e) Date: May 8, 1995

[87] PCT Pub. No.: WO94/13671

PCT Pub. Date: Jun. 23, 1994

[30] Foreign Application Priority Data

Dec. 4, 1992 [EP] European Pat. Off. .............. 92203776

[51] Int. Cl.⁶ ................................................. C07D 223/18
[52] U.S. Cl. ........................................... 514/214; 540/578
[58] Field of Search .............................. 514/214; 540/578

[56] References Cited

U.S. PATENT DOCUMENTS 5,468,743  11/1995  Janssens et al. ........................ 514/214

FOREIGN PATENT DOCUMENTS 0 518 435  12/1992  European Pat. Off. .
WO 92/06981  4/1992  WIPO .

*Primary Examiner*—Joseph McKane
*Attorney, Agent, or Firm*—Ellen Ciambrone Coletti

[57] ABSTRACT

Antiallergic triazolobenzazepines of formula wherein each of the dotted lines independently represents an optional bond; $R^1$ represents hydrogen, halo, $C_{1-4}$alkyl, hydroxy or $C_{1-4}$alkyloxy; $R^2$ represents hydrogen, halo, $C_{1-4}$alkyl, hydroxy or $C_{1-4}$alkyloxy; $R^3$ represents hydrogen, $C_{1-4}$alkyl or halo; —B=D— is a bivalent radical of formula —C($R^4$)=N— (a-1); or —N=C($R^5$)— (a-2); $R^4$ and $R^5$ represent hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl; $R^5$ also represents phenyl or pyridinyl; L represents hydrogen; $C_{1-6}$alkyl; substituted $C_{1-6}$alkyl, $C_{3-6}$alkenyl; $C_{3-6}$alkenyl substituted with aryl or, L represents a radical of formula -Alk-Y-Het¹ (b-1), -Alk-NH—CO—Het² (b-2) or —Alk-Het³ (b-3). Compositions comprising said compounds, processes of preparing the same, and intermediates in the preparation thereof.

14 Claims, No Drawings

TRIAZOLOBENZAZEPINE DERIVATIVES

CROSS-REFERENCE TO RELATED APPLICATIONS

This application is based upon PCT application Ser. No. PCT/EP 93/03320, filed Nov. 25, 1993, which claims priority from European Application Serial No. 92.203.776.7, filed on Dec. 4, 1992.

The present invention is concerned with triazolobenzazepine derivatives having antiallergic activity.

In EP-A-0,339,978 there are described (benzo- or pyrido) cyclohepta heterocyclics which are useful as PAF antagonists, antihistaminics and/or anti-inflammatory agents.

In WO 92/06981 there are described substituted imidazobenzazepines and imidazopyridoazepines having antiallergic and anti-inflammatory activity.

In J. Med. Chem., 26(1983), 974–980 there are described some 1-methyl-4-piperidinylidene-9-substituted pyrrolo[2,1-b][3]benzazepine derivatives having neuroleptic properties.

In DE-27,35,158 there are described triazolobenzazepine derivatives having analgesic activity.

The compounds of the present invention differ structurally from the cited art-known compounds by the fact that the central 7-membered ring invariably contains a nitrogen atom of a fused triazole ring, and by their favorable antiallergic activity.

The present invention is concerned with novel triazolobenzazepines of formula

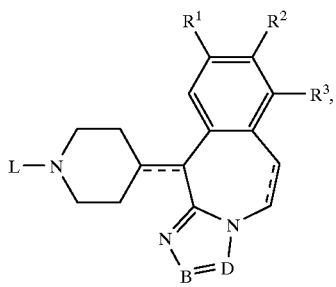

the pharmaceutically acceptable addition salts and stereochemically isomeric forms thereof, wherein
each of the dotted lines independently represents an optional bond;
$R^1$ represents hydrogen, halo, $C_{1-4}$alkyl, hydroxy or $C_{1-4}$alkyloxy;
$R^2$ represents hydrogen, halo, $C_{1-4}$alkyl, hydroxy or $C_{1-4}$alkyloxy;
$R^3$ represents hydrogen, $C_{1-4}$alkyl or halo;
—B═D— is a bivalent radical of formula

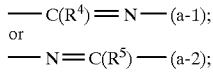

$R^4$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^5$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl, hydroxycarbonyl, phenyl or pyridinyl;

L represents hydrogen; $C_{1-6}$alkyl; $C_{1-6}$alkyl substituted with one substituent selected from the group consisting of hydroxy, $C_{1-4}$alkyloxy, hydroxycarbonyl, $C_{1-4}$alkyloxycarbonyl, $C_{1-4}$alkyloxycarbonyl$C_{1-4}$alkyloxy, hydroxycarbonyl-$C_{1-4}$alkyloxy, $C_{1-4}$alkylaminocarbonylamino, $C_{1-4}$alkylaminothiocarbonylamino, aryl and aryloxy; $C_{1-6}$alkyl substituted with both hydroxy and aryloxy; $C_{3-6}$alkenyl; $C_{3-6}$alkenyl substituted with aryl;
wherein each aryl is phenyl or phenyl substituted with halo, cyano, hydroxy, $C_{1-4}$alkyl, $C_{1-4}$alkyloxy or aminocarbonyl; or, L represents a radical of formula

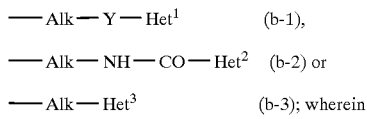

Alk represents $C_{1-4}$alkanediyl;
Y represents O, S or NH;
$Het^1$, $Het^2$ and $Het^3$ each represent furanyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and $Het^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

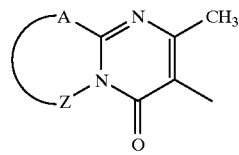

—A—Z— represents —S—CH═CH—, —S—CH$_2$—CH$_2$—, —S—CH$_2$—CH$_2$—CH$_2$—, —CH═CH—CH═CH— or —CH$_2$—CH$_2$—CH$_2$—CH$_2$—.

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, for example, pentyl and hexyl; $C_{3-6}$alkenyl defines straight and branched chain hydrocarbon radicals containing one double bond and having from 3 to 6 carbon atoms such as, for example, 2-propenyl, 2-butenyl, 3-butenyl, 2-methyl-2-propenyl, 2-pentenyl, 3-pentenyl, 3,3-dimethyl-2-propenyl, hexenyl and the like; $C_{C1-4}$alkanediyl defines bivalent straight or branched chain hydrocarbon radicals containing from 1 to 4 carbon atoms such as, for example, methylene, 1,1-ethanediyl, 1,2-ethanediyl, 1,3-propanediyl, 1,4-butanediyl and the like.

The term pharmaceutically acceptable addition salt as used hereinbefore defines the non-toxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are for example, inorganic acids, for example, hydrohalic acid, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) having acidic properties may be converted in a similar manner into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine. The term pharmaceutically acceptable addition salts also comprises the solvates which the compounds of formula (I) may form, e.g. the hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention.

A particular group of compounds are those compounds of formula (I) wherein $R^1$ and $R^2$ each independently are hydrogen, halo, $C_{1-4}$alkyl or $C_{1-4}$alkyloxy.

Interesting compounds are those compounds of formula (I) wherein $R^1$, $R^2$, $R^3$, $R^4$ and $R^5$ represent hydrogen.

Also interesting compounds are those compounds of formula (I) wherein $R^1$, $R^2$ or $R^3$ is halo.

Further interesting compounds of formula (I) are those of formula

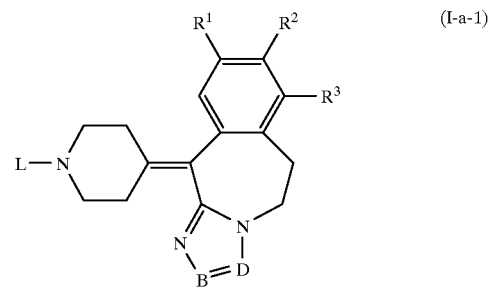

wherein $R^1$, $R^2$, $R^3$, —B═D— and L are as defined under formula (I).

Yet another group of interesting compounds are those compounds of formula (1) wherein —B═D— is a bivalent radical of formula —C($R^4$)═N—(a-1).

Preferred compounds are those compounds of formula (I) wherein L represents $C_{1-4}$alkyl or a radical of formula Alk-Het³ (b-3).

More preferred compounds are those preferred compounds wherein L, is methyl, pyridinyl, 2-oxo-3-oxazolidinyl or a radical of formula

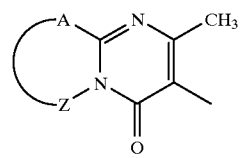

The most preferred compound is:

6,11-dihydro-11-(1-methyl-4-piperidinylidene)-5H-1,2,4-triazolo[5,1-b][3]benzazepine, the stereoisomers and the pharmaceutically acceptable acid-addition salts thereof.

In the following paragraphs there are described different ways of preparing the compounds of formula (I). In order to simplify the structural formulae of the compounds of formula (I) and the intermediates intervening in their preparation, the triazolobenzazepine moiety will be represented by the symbol T hereinafter.

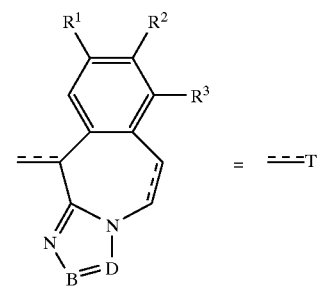

The compounds of formula (I) can be prepared by cyclizing an alcohol of formula (II) or a ketone of formula (III).

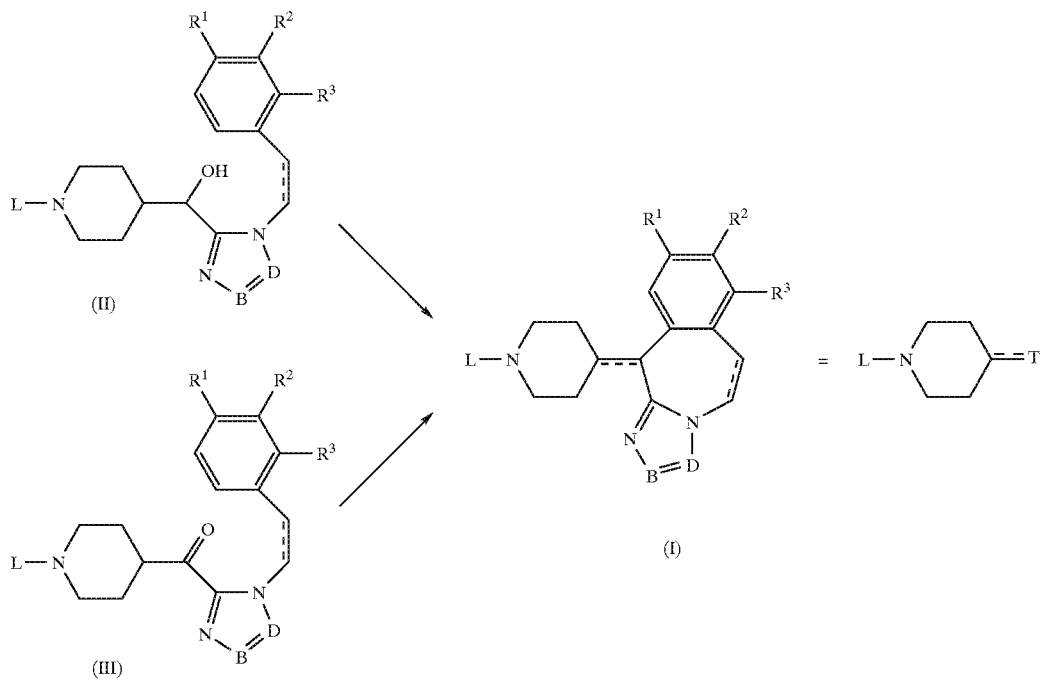

Said cyclization reaction is conveniently conducted by treating the intermediate of formula (II) or (III) with an appropriate acid, thus yielding a reactive intermediate which cyclizes to a compound of formula (I). Appropriate acids are, for example, strong acids, in particular superacid systems, e.g. methanesulfonic acid, trifluoromethanesulfonic acid, trifluoroacetic acid, methanesulfonic acid/boron trifluoride, hydrofluoric acid/boron trifluoride, or Lewis acids, e.g. aluminum chloride and the like. Obviously, only those compounds of formula (I) wherein L is stable under the given reaction conditions can be prepared according to the above reaction procedure.

In the foregoing and following preparations, the reaction mixture is worked up following art-known methods and the reaction product is isolated and, if necessary, further purified.

The compounds of formula (I) wherein the central ring of the tricyclic moiety does not contain an optional bond may also be prepared by cyclizing an intermediate of formula (IV).

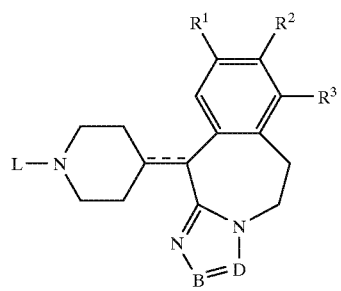

In formula (IV) and hereinafter W represents an appropriate leaving group such as, for example, halo, e.g. chloro, bromo and the like; or a sulfonyloxy group such as, for example, methansulfonyloxy, 4-methylbenzenesulfonyloxy and the like. Said cyclization reaction can conveniently be conducted in a reaction-inert solvent such as, for example, an aromatic hydrocarbon, an alkanol, a ketone, an ether, a dipolar aprotic solvent, a halogenated hydrocarbon or a mixture of such solvents. The addition of an appropriate base such as, for example, an alkali or an earth alkaline metal carbonate, hydrogen carbonate, alkoxide, hydride, amide, hydroxide or oxide; or an organic base, such as, for example, an amine, may be utilized to pick up the acid which is liberated during the course of the reaction. In some instances the addition of an iodide salt, preferably an alkali metal iodide, is appropriate. Somewhat elevated temperatures and stirring may enhance the rate of the reaction.

Alternatively, the compounds of formula (I) wherein a double bond exists between the piperidinyl and the triazolobenzazepine moiety, said compounds being represented by formula (I-a), can be prepared by dehydrating an alcohol of formula (V) or (VI).

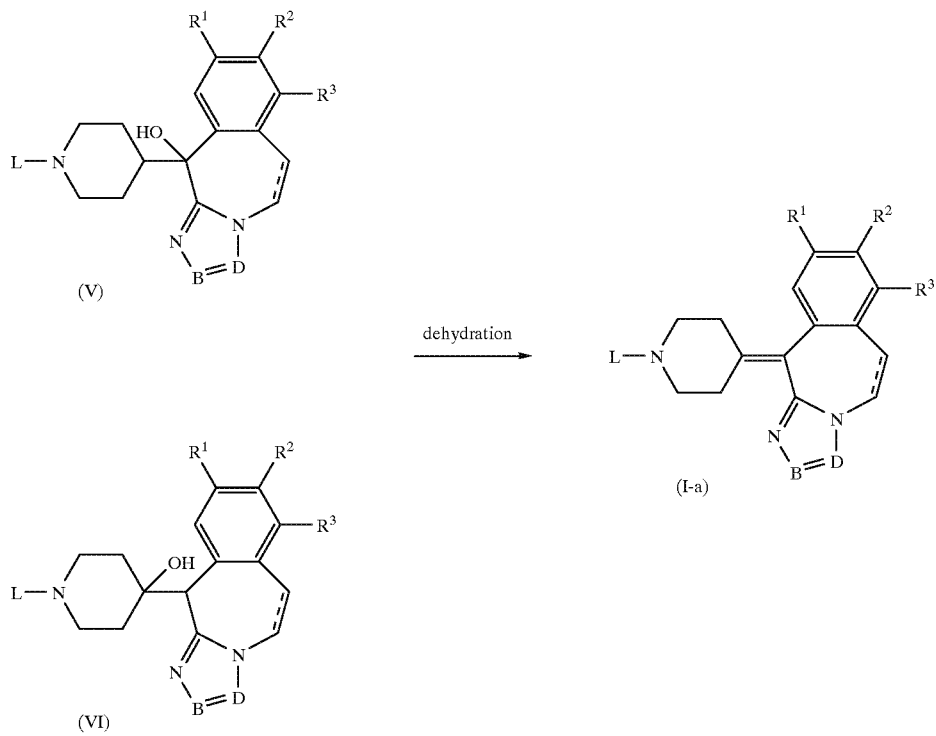

Said dehydration reaction can conveniently be conducted employing conventional dehydrating reagents following art-known methodologies. Appropriate dehydrating reagents are, for example, acids, e.g. sulfuric acid, phosphoric acid, hydrochloric acid, methanesulfonic acid, carboxylic acids, e.g. acetic acid, trifluoroacetic acid and mixtures thereof; anhydrides, e.g. acetic anhydride, phosphorus pentoxide and the like; other suitable reagents, e.g. zinc chloride, thionyl chloride, boron trifluoride etherate, phosphoryl chloride, potassium bisulfate, potassium hydroxide. In some instances said dehydration reaction may require heating the reaction mixture, more particularly up to the reflux temperature. Again, only those compounds of formula (1-a) wherein L is stable under the given reaction conditions can be prepared according to the above reaction procedure.

The compounds of formula (I-a) may be converted into the compounds of formula (I-b) upon catalytic hydrogenation following art-known procedures.

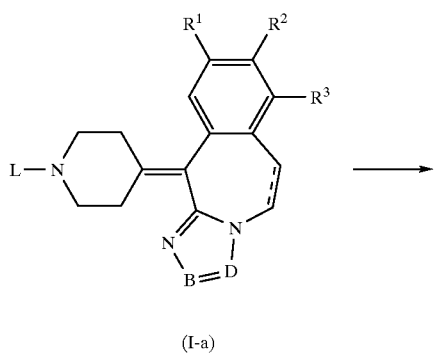

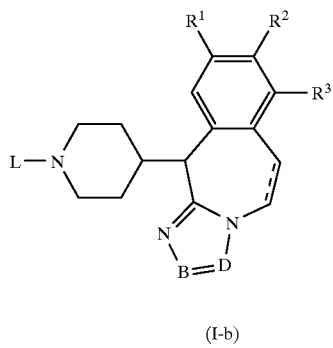

(I-b)

The compounds of formula (I) wherein L is $C_{1-6}$alkyl, said compounds being represented by the formula (I-c) can be converted into the compounds of formula (I), wherein L is hydrogen, said compounds being represented by the formula (I-d) in a number of manners. A first method involves dealkylating - carbonylating the compounds of formula (I-c) with a $C_{1-4}$alkylchloroformate and subsequently hydrolyzing the thus obtained compound of formula (VII-a).

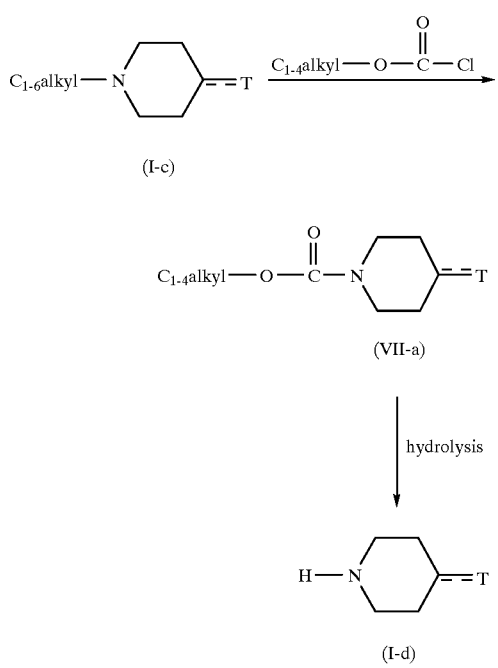

The reaction with the $C_{1-4}$alkylchloroformate is conveniently conducted by stirring and heating the starting material (I-c) with the reagent in an appropriate solvent and in the presence of a suitable base. Appropriate solvents are, for example, aromatic hydrocarbons, e.g. methylbenzene, dimethylbenzene, chlorobenzene; ethers, e.g. 1,2-dimethoxyethane, and the like solvents. Suitable bases are, for example, alkali or earth alkaline metal carbonates, hydrogen carbonates, hydroxides, or organic bases such as, N,N-diethylethanamine, N-(1-methylethyl)-2-propanamine, and the like. The compounds of formula (VII-a) are hydrolyzed in acidic or basic media following conventional methods. For example, concentrated acids such as hydrobromic, hydrochloric acid or sulfuric acid can be used, or alternatively bases such as alkali metal or earth alkaline metal hydroxides in water, an alkanol or a mixture of water-alkanol may be used. Suitable alkanols are methanol, ethanol, 2-propanol and the like. In order to enhance the rate of the reaction it is advantageous to heat the reaction mixture, in particular up to the reflux temperature.

The compounds of formula (I-c) may also be converted directly into the compounds of formula (I-d) by stirring and heating them with an α-halo-$C_{1-4}$alkyl chloroformate in an appropriate solvent such as, for example, a halogenated hydrocarbon, e.g. dichloromethane, trichloromethane; an aromatic hydrocarbon, e.g. methylbenzene, dimethylbenzene; an ether, e.g. 1,2-dimethoxyethane; an alcohol, e.g. methanol, ethanol, 2-propanol, optionally in the presence of a base such as, for example, an alkali or earth alkaline metal carbonate, hydrogen carbonate, hydroxide or an amine, e.g. N,N-diethylethanamine, N-(1-methylethyl)-2-propanamine, and the like.

The compounds of formula (I-d) can also be prepared by debenzylating a compound of formula (I-e) by catalytic hydrogenation in the presence of hydrogen and an appropriate catalyst in a reaction-inert solvent.

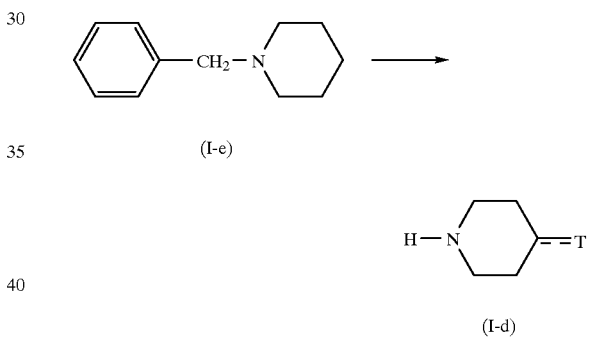

A suitable catalyst in the above reaction is, for example, platinum-on-charcoal, palladium-on-charcoal, and the like. An appropriate reaction-inert solvent for said debenzylation reaction is, for example, an alcohol, e.g. methanol, ethanol, 2-propanol and the like, an ester, e.g. ethylacetate and the like, an acid, e.g. acetic acid and the like.

The compounds of formula (I) wherein L is other than hydrogen, said compounds being represented by formula (I-f) and said L by $L^1$, can be prepared by N-alkylating the compounds of formula (I-d) with a reagent of formula $L^1$-W (VIII).

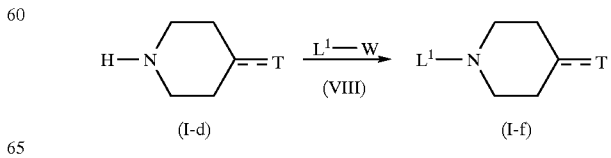

Said N-alkylation reaction can conveniently be conducted in a reaction-inert solvent such as, for example, an aromatic hydrocarbon, an alkanol, a ketone, an ether, a dipolar aprotic solvent, a halogenated hydrocarbon, or a mixture of such solvents. The addition of an appropriate base such as, for example, an alkali or an earth alkaline metal carbonate, hydrogen carbonate, alkoxide, hydride, amide, hydroxide or oxide, or an organic base, such as, for example, an amine, may be utilized to pick up the acid which is librated-during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

The compounds of formula (I) wherein L is $C_{1-6}$alkyl or substituted $C_{1-6}$alkyl can also be prepared by reductive N-alkylation of the compounds of formula (I-d) following art-known procedures. The compounds of formula (I) wherein L is $C_{1-6}$alkyl or substituted $C_{1-6}$alkyl can further be prepared by the addition reaction of the compounds of formula (I-d) with a suitable alkene following art-known procedures. The compounds of formula (I) wherein L is $C_{1-6}$alkyl substituted with hydroxy can be prepared by reacting a compound of formula (I-d) with a suitable epoxide following art-known procedures.

The compounds of formula (I) wherein $R^4$ or $R^5$ is hydroxy$C_{1-4}$alkyl may be prepared by reacting the corresponding compound of formula (I) wherein $R^4$ or $R^5$ is hydrogen with an aldehyde, e.g. formaldehyde, in the presence of an acid, e.g. acetic acid.

The compounds of formula (I) may further be converted into each other following art-known functional group transformation procedures.

Some examples of such procedures are cited hereinafter. The compounds of formula (I) containing a cyano substituent can be converted into the corresponding amine, upon reaction in a hydrogen containing medium in the presence of an appropriate catalyst such as, for example, Raney nickel and the like. Amino groups may be N-alkylated or N-acylated following art-known procedures. Further, the compounds of formula (I) containing ester groups may be converted in the corresponding carboxylic acids by art-known hydrolysis procedures. Aromatic ethers may be converted into the corresponding alcohols following art-known ether cleavage procedures.

The compounds of formula (VII-a) intervening in the preparations described hereinbefore are novel and have especially been developed for use as intermediates in said preparations. Consequently, the present invention also relates to novel compounds of formula

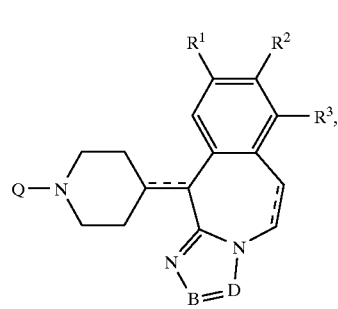

the addition salt forms thereof and the stereochemically isomeric forms thereof, wherein each of the dotted lines independently represents an optional bond, $R^1$, $R^2$, $R^3$ and —B=D— are as defined under formula (I); and Q is $C_{1-6}$alkyloxycarbonyl, $C_{1-4}$alkylcarbonyl or $C_{1-6}$alkyl substituted with halo, cyano, amino or methylsulfonyloxy;

Particularly interesting compounds of formula (VII) are those wherein Q represents $C_{1-6}$alkyloxycarbonyl or $C_{1-6}$alkyl substituted with cyano or amino, the addition salts thereof and the stereochemically isomeric forms thereof.

In the following paragraphs there are described several methods of preparing the starting materials employed in the foregoing preparations.

The intermediates of formula (II) can be prepared from the corresponding ketones of formula (III) by reduction.

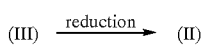

Said reduction can conveniently be conducted by reacting the starting ketone (III) with hydrogen in a solvent such as, for example, an alcohol, e.g. methanol, ethanol; an acid, e.g. acetic acid; an ester, e.g. ethyl acetate; in the presence of a hydrogenation catalyst, e.g. palladium-on-charcoal, platinum-on-charcoal, Raney Nickel. In order to enhance the rate of the reaction, the reaction mixture may be heated and, if desired, the pressure of the hydrogen gas may be raised.

Alternatively, the alcohols of formula (II) can also be prepared by reducing the ketones (III) with a reducing agent such as, for example, lithium aluminum hydride, sodium borohydride, sodium cyanoborohydride and the like in a suitable solvent such as, for example, an ether, e.g. 1,1'-oxybisethane, tetrahydrofuran and the like; an alcohol, e.g. methanol, ethanol and the like.

The ketones of formula (III) can be prepared by the addition of a compound of formula (IX) to a reagent of formula (X).

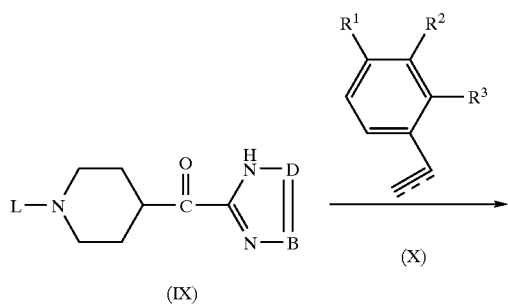

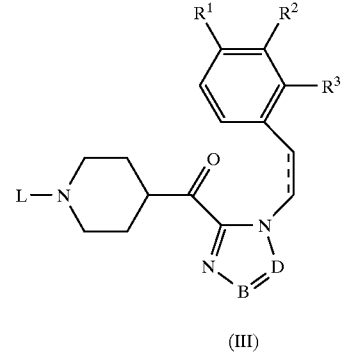

The ketones of formula (III) wherein the dotted line is not an optional bond can be prepared by N-alkylating an intermediate of formula (IX) with a reagent of formula (XI) wherein W represents a reactive leaving group as defined hereinbefore.

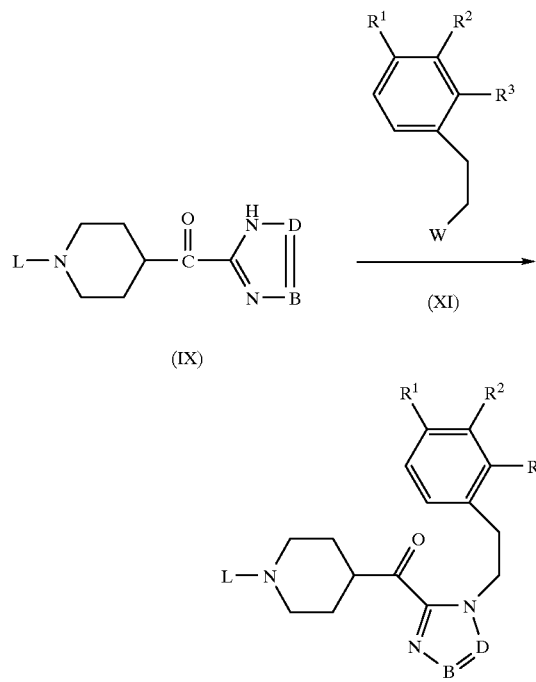

Said N-alkylation reaction can conveniently be conducted following the procedures employed in preparing the compounds of formula (I-f) from the compounds of formula (I-d).

The intermediates of formula (V) can be prepared by addition of a Grignard reagent (XII) to a ketone of formula (XIII) in a reaction-inert solvent, e.g. tetrahydrofuran.

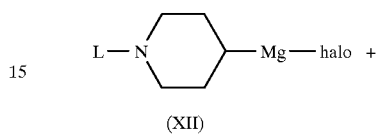

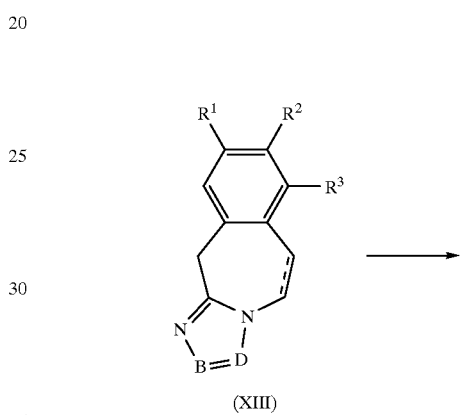

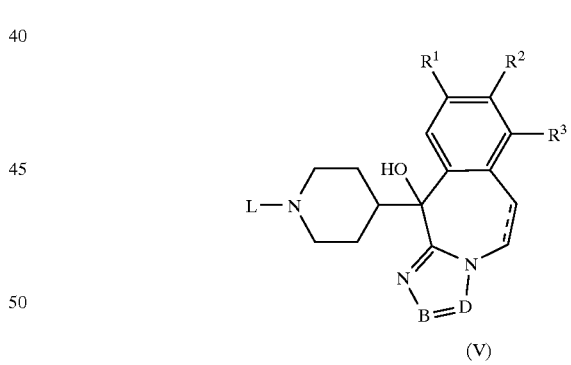

The tricyclic ketones of formula (XIII) in turn are prepared from intermediates of formula (XIV) or (XV) by oxidation with a suitable oxidizing reagent in a reaction-inert solvent.

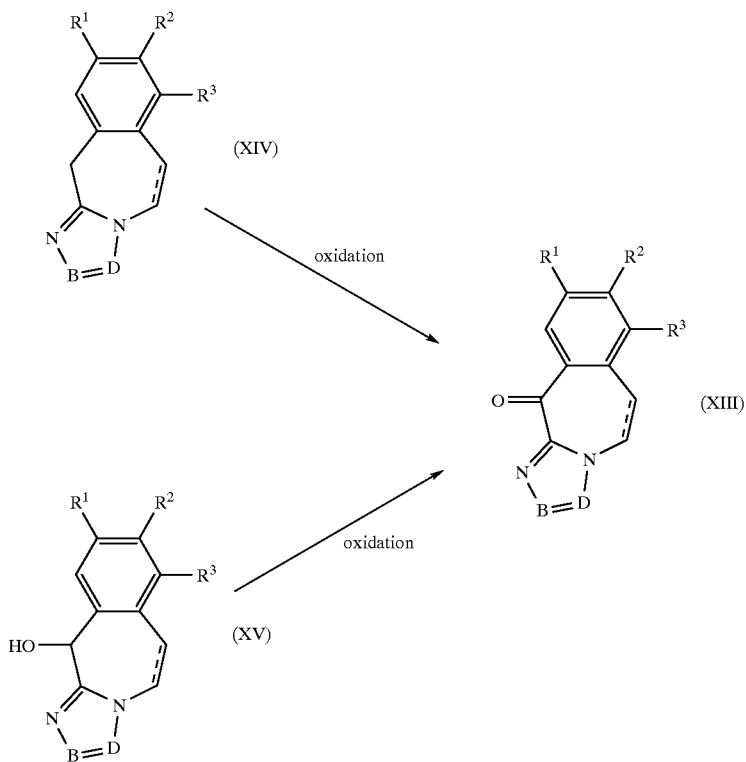

Suitable oxidizing reagents are, for example, manganese dioxide, selenium dioxide, ceric ammonium nitrate and the like. Reaction-inert solvents are, for example, a halogenated hydrocarbon, e.g. dichloromethane, or a dipolar aprotic solvent, e.g. N,N-dimethylformamide.

The compounds of formula (XIV) wherein the dotted lines do not represent an optional bond, can be prepared from the corresponding compounds of formula (XIV) wherein said dotted lines do represent an optional bond, following art-known hydrogenation procedures, e.g. by reaction with hydrogen in the presence of a hydrogenation catalyst.

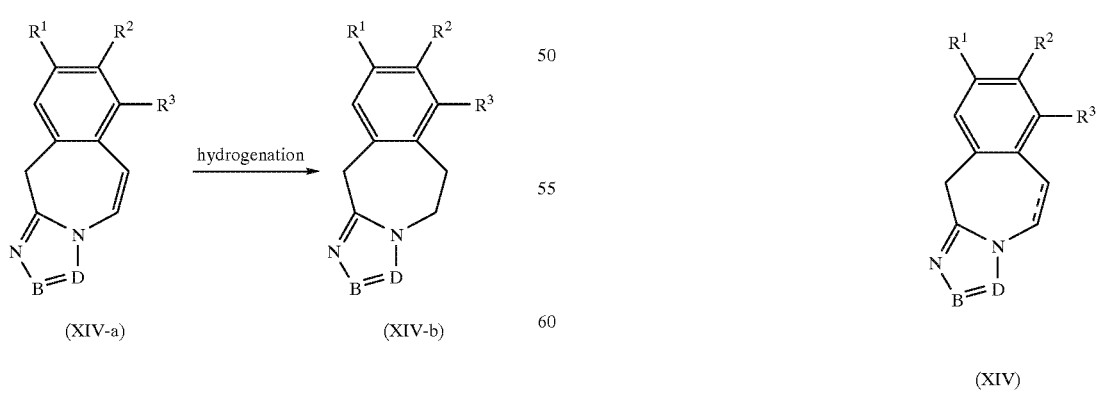

The intermediates of formula (XIV) can be prepared from cyclization of an intermediate of formula (XVI).

Said cyclization reaction is conveniently conducted in the presence of a Lewis acid, e.g. aluminum chloride, and the like. In some instances it may be appropriate to supplement the reaction mixture with a suitable amount of sodium chloride.

The intermediates of formula (XV) can be prepared from the cyclization of an intermediate of formula (XVII) in the presence of an acid, e.g. methanesulfonic acid.

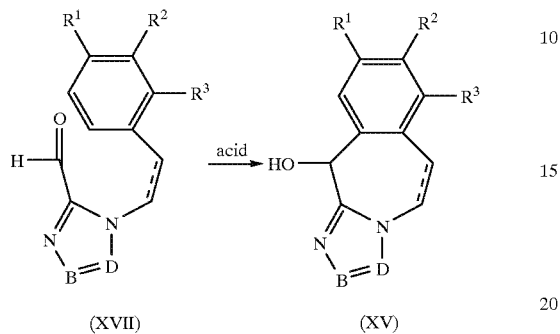

The intermediates of formula (V) can also be prepared from the cyclization of an intermediate of formula (III) in the presence of an acid in a reaction inert solvent.

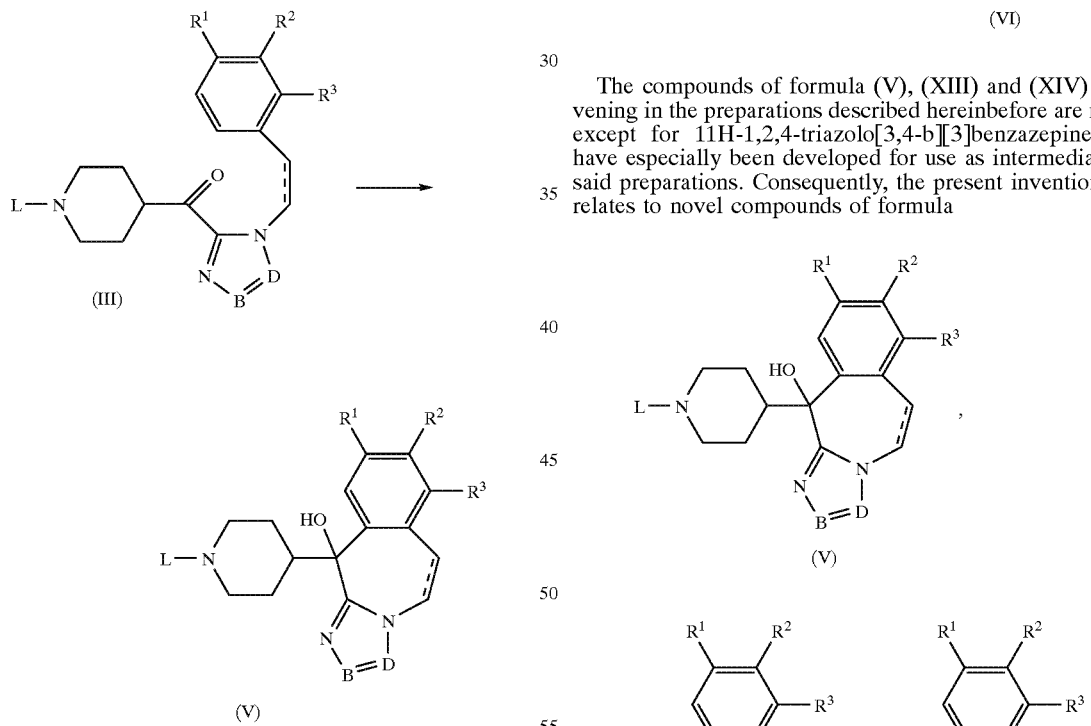

An appropriate acid in the above reaction is, for example, a Lewis acid, e.g. tin(IV)chloride, aluminum trichloride and the like. A suitable reaction-inert solvent is, for example, a halogenated hydrocarbon, e.g. dichloromethane, 1,2-dichloroethane, and the like.

The intermediates of formula (VI) can be prepared by reaction of a ketone of formula (XVIII) with an intermediate of formula (XIV) in the precence of e.g. lithium diisopropylamide in a reaction-inert solvent, e.g. tetrahydrofuran.

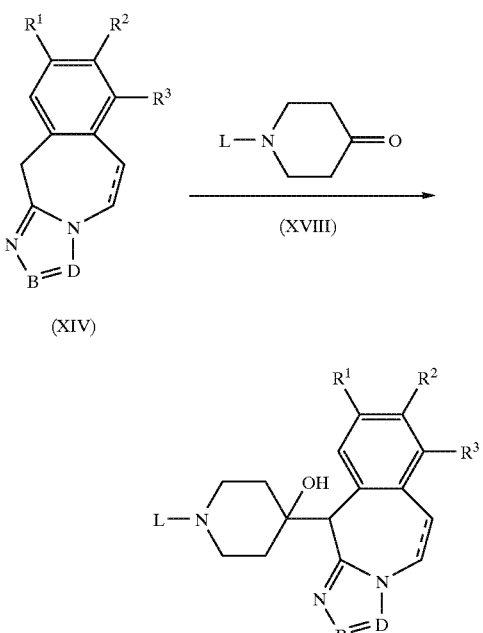

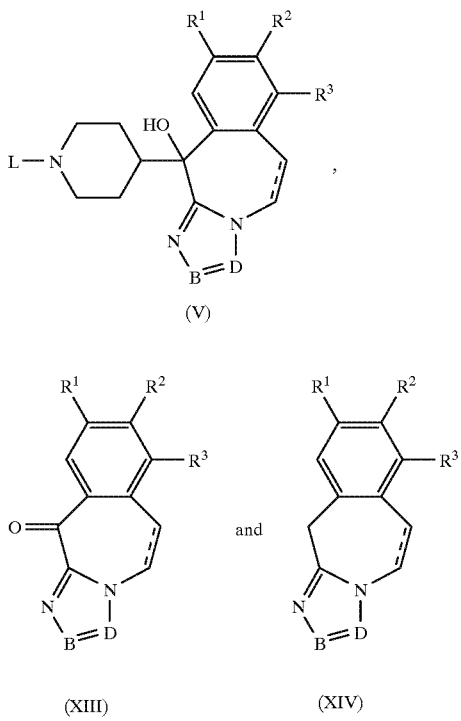

The compounds of formula (V), (XIII) and (XIV) intervening in the preparations described hereinbefore are novel, except for 11H-1,2,4-triazolo[3,4-b][3]benzazepine, and have especially been developed for use as intermediates in said preparations. Consequently, the present invention also relates to novel compounds of formula the addition salt forms thereof and the stereochemically isomeric forms thereof, wherein L, $R^1$, $R^2$, $R^3$ and —B=D— are as defined under formula (I), provided that 11H-1,2,4-triazolo[3,4-b][3]benzazepine is excluded.

The compounds of formula (I) and some of the compounds of formula (VII), in particular those wherein Q is $C_{1-6}$alkyloxycarbonyl or $C_{1-6}$alkyl substituted with cyano or amino, the addition salts and stereochemically isomeric forms thereof possess useful pharmacological properties. In particular they are active antiallergic agents, which activity can clearly be demonstrated by he test results obtained in a number of indicative tests. Antihistaminic activity can be demonstrated in 'Protection of Rats from Compound 48/80—induced Lethality' test (Arch. Int. Pharmacodyn. Ther., 234, 164–176, 1978). The $ED_{50}$-values for compounds 1–8, 10, 16, 20–33, 36–38, 40–42, 44 and 45 were found to be equal or below 0.31 mg/kg.

An advantageous feature of the compounds of the present invention resides in their excellent oral activity; the present compounds when administered orally have been found to be practically equipotent with the same being administered subcutaneously.

An interesting feature of the present compounds relates to their fast onset of action and the favorable duration of their action.

In view of their antiallergic properties, the compounds of formula (I) and (VII) and their acid addition salts are very useful in the treatment of broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Addition salts of the subject compounds due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) and (VII) or a pharmaceutically acceptable addition salt form thereof.

In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects.

Experimental Part

A. Preparation of the intermediate compounds

EXAMPLE 1 a) A solution of butyllithium in hexane (119 ml) was added dropwise at −70° C. under nitrogen to a solution of N-(1-methylethyl)-2-propanamine (26.7 ml) in tetrahydrofuran (280 ml) and the mixture was stirred for 30 minutes. 1-(2-phenylethyl)-1,2,4-triazole (0.173 mol) in tetrahydrofuran (20 ml) was added and the mixture was stirred at −70° C. for 1 hour. N,N-dimethylformamide (17.4 ml) was added dropwise and the mixture was stirred at −70° C. for 1 hour and then at room temperarure for 2 hours. The mixture was poured into ice water and extracted with 1,1'-oxybisethane. The organic layer was dried ($MgSO_4$), filtered off and evaporated. The residue (11.7 g) was purified by column chromatography over silica gel (eluent: $CH_2Cl_2/CH_3OH/NH_4OH$ 99/1/0.1) (35–70 μm). The pure fractions were collected and evaporated, yielding 7g (40%) of 2-(2-phenylethyl)-2H-1,2,4-triazole-3-carboxaldehyde (interm. 1).

In a similar way there were prepared:

2-[2-(3-fluorophenyl)ethyl]-2H-1,2,4-triazole-3-carboxaldehyde; mp.87.5° C. (interm. 2);

2-[2-(4-chlorophenyl)ethyl]-2H-1,2,4-triazole-3-carboxaldehyde (interm. 3);

[2-[2-(3-methoxyphenyl)ethyl]-2H-1,2,4-triazol-3-yl](1-methyl-4-piperidinyl)methanone (interm. 4); and

[2-[2-(2-methylphenyl)ethyl]-2H-1,2,4-triazol-3-yl](1-methyl-4-piperidinyl)methanone (interm. 5);

b) Intermediate (1) (0.0398 mol) in methanesulfonic acid (30 ml) was stirred at room temperature for 3 hours. The mixture was poured into ice, basified with ammonia and extracted with dichloromethane. The organic layer was dried ($MgSO_4$), filtered off and evaporated. The residue (37.3 g) was purified by column chromatography over silica gel (eluent: $CH_2Cl_2/C_3OH/NH_4OH$ 98/2/0.1) (35–70 μm). The pure fractions were collected and evaporated, yielding 14 g (47%) of (±)-6,11-dihydro-5H-1,2,4-triazolo-[5,1-b][3] benzazepin-11-ol (interm. 6).

In a similar manner there were prepared:

(±)-8-fluoro-6,11-dihydro-5H-[1,2,4]triazolo[5,1-b][3] benzazepin-11-ol; mp. 179.8° C. (interm. 7); and (±)-9-chloro-6,11-dihydro-5H-[1,2,4]triazolo[5,1-b][3] benzazepin-11-ol; mp. 138.8° C. (interm. 8).

c) A mixture of intermediate (6) (0.0235 mol) and manganese dioxide (50 g) in N,N-dimethylformamide (30 ml) was heated at 40° C. for 2 hours and then stirred at room temperature overnight. The mixture was filtered over celite and washed with methanol. The filtrate was evaporated till dryness. The residue (10.58 g) was purified by column chromatography over silica gel (eluent: $CH_2Cl_2/CH_3OH$ 98/2) (35–70 μm). The pure fractions were collected and evaporated. The residue (8.95 g) was crystallized from 2,2'-oxybispropane, yielding 7.16 (77%) of 5,6-dihydro-11H-1,2,4-triazolo[5,1-b]-[3]benzazepin-1 1-one (interm. 9).

In a similar way there were prepared:
8-fluoro-5,6-dihydro-11H-[1,2,4]triazolo[5,1-b][3]benzazepin-11-one (interm. 10); and
9-chloro-5,6-dihydro-11H-[1,2,4]triazolo[5,1-b][3]benzazepin-11-one; mp. 160.6° C. (interm. 11).

EXAMPLE 2 a) A mixture of 1H-4,5-dihydro-benzazepine-2-amine (0.068 mol) and formic acid hydrazide (12.25 g) in methanol (980 ml) was stirred and refluxed for 72 hours. The mixture was evaporated in vacuo. The residue was taken up in potassium carbonate 5% (150 ml) and extracted with dichloromethane. The organic layer was washed with water, dried ($MgSO_4$), filtered off and evaporated. The residue (9.9 g) was purified by column chromatography over silica gel (eluent: $CH_2Cl_2/CH_3OH$ 95/5). The pure fractions were collected and evaporated, yielding 8.8 g (70%) of product. A sample (1.9 g) was crystallized from 2,2'-oxybispropane, yielding 1.6 g of 6,11-dihydro-5H-1,2,4-triazolo[3,4-b][3]benzazepine; mp. 191.4° C. (interm. 12).

In a similar way there were prepared:
6,11-dihydro-3-phenyl-5H-1,2,4-triazolo[3,4-b][3]benzazepine (interm. 13);
6,11-dihydro-3-methyl-5H-1,2,4-triazolo[3,4-b][3]benzazepine (interm. 14); and
6,11-dihydro-3-(4-pyridinyl)-5H-1,2,4-triazolo[3,4-b][3]benzazepine; mp. 214.4° C. (interm. 15).

b) A mixture of intermediate (12) (0.035 mol) and manganese dioxide (64.4 g) in N,N-dimethylformamide (220 ml) was stirred vigorously for 24 hours at 40° C. The mixture was filtered hot over celite, washed with hot N,N-dimethylformamide and evaporated in vacuo at 80° C. The residue was taken up in 2,2'-oxybispropane and filtered off. The precipitate was washed with 2,2'-oxybispropane and dried, yielding 5.8 g (83%) of product. A sample (2.1 g) was recrystallized from methanol, yielding 0.92 g of 5,6-dihydro-11H-1,2,4-triazolo[3,4-b][3]benzazepin-11-one; mp. 187.2° C. (interm. 16).

In a similar way there were prepared:
11H-1,2,4-triazolo[3,4-b][3]benzazepin-11-one (interm. 17);
5,6-dihydro-3-phenyl-11H-1,2,4-triazolo[3,4-b][3]benzazepin-11-one; mp. 188.3° C. (interm. 18);
5,6-dihydro-3-methyl-11H-1,2,4-triazolo[3,4-b][3]benzazepin-11-one (interm. 19); and
5,6-dihydro-3-(4-pyridinyl)-11H-1,2,4-triazolo[3,4-b][3]benzazepin-11-one (interm. 20);

EXAMPLE 3

Magnesium turnings (1.91 g) and 1,2-dibromoethane (3 drops) were stirred in tetrahydrofuran (few ml). 4-Chloro-1-methylpiperidine (few ml) was added and when the reaction was started, 4-chloro-1-methylpiperidine (9.52 g) in tetrahydrofuran (40 ml) was added dropwise and the mixture was brought till reflux. The mixture was refluxed for 2 hours, intermediate (9) (0.036 mol) in tetrahydrofuran (90 ml) was added at 60° C. and the mixture was refluxed for 3 hours. The mixture was cooled, poured into a mixture of ammonium chloride/ice and extracted. The aqueous layer was extracted with dichloromethane and methanol. The organic layer was dried ($MgSO_4$), filtered off and evaporated. The residue (16.5 g) was purified by column chromatography over silica gel (eluent: $CH_2Cl_2/CH_3OH/NH_4OH$ 95/5/0.05) (15 μm). The pure fractions were collected and evaporated, yielding 4.14 g (39%) (±)-6,11-dihydro-11-(1-methyl-4-piperidinyl)-5H-1,2,4-triazolo[5,1-b][3]benzazepin-11-ol (interm. 21).

In a similar way there were prepared:
(±)-8-fluoro-6, 11-dihydro-11-(1-methyl-4-piperidinyl)-5H-[1,2,4]triazolo[5,1-b]-[3]benzazepin-1 1-ol (interm. 22);
(±)-11-(1-methyl-4-piperidinyl)-11H-1,2,4-triazolo[ 3,4-b][3]benzazepin-11-ol (interm. 23);
(±)-6,11-dihydro-11-(1-methyl-4-piperidinyl)-5H-1,2,4-triazolo[3,4-b][3]benzazepin-11-ol (interm. 24);
(±)-6, 11-dihydro-11-(1-methyl-4-piperidinyl)-3-phenyl-5H-1,2,4-triazolo[3,4-b][3]-benzazepin-11-ol (interm. 25);
(±)-6,11-dihydro-3-methyl-11-(1-methyl-4-piperidinyl)-5H-1,2,4-triazolo[3,4-b][3]-benzazepin-11-ol (interm. 26);
(±)-6,11-dihydro-11-(1-methyl-4-piperidinyl)-3-(4-pyridinyl)-5H-1,2,4-triazolo[3,4-b]-[3]benzazepin-11-ol (interm. 27); and
(±)-9-chloro-6,11-dihydro-11-(1-methyl-4-piperidinyl)-5H-[ 1,2,4]triazolo[5,1-b]-[3]benzazepin-11-ol (interm. 28).

EXAMPLE 4

A mixture of intermediate (5) (0.098 mol) and aluminum trichloride (65.35 g) in 1,2-dichloroethane (400 ml) was stirred at room temperature overnight. The mixture was poured into ice water and basified with ammonia. The minerals were filtered over celite and extracted with dichloromethane. The organic layer was dried ($MgSO_4$), filtered off and evaporated. The residue (25 g) was purified by column chromatography over silica gel (eluent: $CH_2Cl_2/CH_3OH/NH_4OH$ 96/4/0.2) (15–40 μm). Fraction 1 was collected and evaporated. The residue was crystallized from 2,2'-oxybispropane, yielding 1.33 (4%) of (±)-6,11-dihydro-7-methyl-11-(1-methyl-4-piperidinyl)-5H-[1,2,4]triazolo-[5,1-b][3]benzazepin-11-ol; mp. 190.8° C. (interm. 29).

B. Preparation of the final compounds

EXAMPLE 5

A mixture of intermediate (4) (0.127 mol) in methanesulfonic acid (220 ml) was stirred and refluxed overnight. The mixture was cooled, poured into ice, basified with ammonia and extracted with dichloromethane. The organic layer was dried ($MgSO_4$), filtered off and evaporated. The residue (44.8 g) was purified by column chromatography over silica gel (eluent: $CH_2Cl_2/CH_3OH/NH_4OH$ 90/10/0.5 to 80/20/0.5) (15–40 μm). The pure fractions were collected and evaporated. Fraction 1 (8.8 g) was recrystallized from 2-butanone/2,2'-oxybispropane, yielding 3.8 g (20%) of 6,11-dihydro-8-methoxy-11-(1-methyl-4-piperidinylidene)-5H-[ 1,2,4]triazolo[5,1-b][3]benzazepine; mp. 165.6° C. (comp. 1). Fraction 2 (6 g) was crystallized from methanol /2,2'-oxybispropane, yielding 5.1 g (16%) 6,11-dihydro-1-(1-methyl-4-piperidinylidene)-5H-[1,2,4]triazolo[5,1-b][3]benzazepin-8-ol; mp. 285.3° C. (comp. 2).

EXAMPLE 6

A mixture of intermediate (5) (0.098 mol) and aluminum trichloride (65.35 g) in 1,2-dichloroethane (400 ml) was stirred at room temperature overnight. The mixture was poured into ice water and basified with ammonia. The minerals were filtered over celite and extracted with dichloromethane. The organic layer was dried (MgSO$_4$), filtered off and evaporated. The residue (25 g) was purified by column chromatography over silica gel (eluent: CH$_2$Cl$_2$/CH$_3$OH/NH$_4$OH 96/4/0.2) (15–40 µm). Fraction 1 was collected and evaporated. The residue was crystallized from 2,2'-oxybispropane, yielding 1.33 g (4%) of (±)-6,11-dihydro-7-methyl-11-(1-methyl-4-piperidinyl)-5H-[1,2,4]triazolo[5,1-b][3]benzazepin-11-ol. Fraction 2 was collected and evaporated. The residue (14.2 g) was recrystallized from 2,2'-oxybispropane, yielding 6.66 g (49%) of 6,11-dihydro-7-methyl-11-(1-methyl-4-piperidinylidene)-5H-[1,2,4]triazolo[5,1-b][3]benzazepine; mp. 150.2° C. (comp. 3).

EXAMPLE 7

A mixture of intermediate (28) (0.006 mol) in phosphoryl chloride (80 ml) was stirred and refluxed for 24 hours. The mixture was evaporated, the residue was taken up in ice water and ethyl acetate, basified with sodium hydroxide and extracted with ethyl acetate. The organic layer was washed with water, dried (MgSO$_4$), filtered off and evaporated till dryness. The residue was purified by column chromatography over silica gel (eluent: CH$_2$Cl$_2$/CH$_3$OH/NH$_4$OH 95/5/0.5). The pure fractions were collected and evaporated, yielding 1.5 g (80%). The product was crystallized from 2,2'-oxybispropane, yielding 1.04 g (55%) (±)-9-chloro-6,11-dihydro-11-(1-methyl-4-piperidinylidene)-5H-[1,2,4]-triazolo[5,1-b][3]benzazepine; mp. 176.2° C. (comp. 4).

EXAMPLE 8 a) A mixture of intermediate (21) (0.0139 mol) in sulfuric acid (40 ml) was heated at 80° C. for 1 hour. The mixture was cooled, poured into ice water, basified with ammonia and extracted with dichloromethane. The organic layer was dried (MgSO$_4$), filtered off and evaporated. The residue (2.28 g) was purified by column chromatography over silica gel (eluent: CH$_2$Cl$_2$/CH$_3$OH/NH$_4$OH 95/5/0.1 to 90/10/0.1) (15 µm). The pure fractions were collected and evaporated. The residue (1.93 g) was crystallized from 2,2'-oxybispropane, yielding 1.36 g (49%) of 6,11-dihydro-11-(1-methyl-4-piperidinylidene)-5H-1,2,4-triazolo[5,1-b][3]benzazepine; mp. 126.8° C. (comp. 5).

In a similar way there were prepared:

8-fluoro-6,11-dihydro-11-(1-methyl-4-piperidinylidene)-5H-[1,2,4-triazolo[5,1-b]-[3]benzazepine; mp. 146.2° C. (comp. 6);

11-(1-methyl-4-piperidinylidene)-11H-1,2,4-triazolo[3,4-b][3]benzazepine; mp. 252.2° C. (comp. 7);

6,11-dihydro-11-(1-methyl-4-piperidinylidene)-5H-1,2,4-triazolo[3,4-b][3]benzazepine; mp. 213.8° C. (comp. 8);

6,11-dihydro-1-(1-methyl-4-piperidinylidene)-3-phenyl-5H-1,2,4-triazolo[3,4-b]-[3]benzazepine; mp. 221.5° C. (comp. 9);

6,11-dihydro-3-methyl-11-(1-methyl-4-piperidinylidene)-5H-1,2,4-triazolo[3,4-b][3]benzazepine; mp. 226.7° C. (comp. 10); and 6,11-dihydro-11-(I -methyl-4-piperidinylidene)-3-(4-pyridinyl)-5H-1,2,4-triazolo[3,4-b][3]benzazepine; mp. 239.6° C. (comp. 11).

EXAMPLE 9 a) Carbonochloridic acid ethyl ester (34.1 ml) was added dropwise at 80° C. to a solution of compound (5) (0.0446 mol) in N,N-diethylethanamine (12.4 ml) and methylbenzene (800 ml) and the mixture was stirred and refluxed for 2 hours. The mixture was cooled, poured into water, decanted off and extracted with ethyl acetate. The organic layer was washed with water, dried (MgSO$_4$), filtered off and evaporated. The residue was used without further purification, yielding 19.3 g (100%) of product. A sample (2 g) was purified by column chromatography over silica gel (eluent: CH$_2$Cl$_2$/CH$_3$OH/NH$_4$OH 96/4/0.1) (15 µm). The pure fractions were collected and evaporated. The residue was recrystallized from 2-propanol/ 2,2'-oxybispropane, yielding 1 g of ethyl 4-(5,6-dihydro-11H-[1,2,4]triazolo[5,1-b][3]benzazepin-11-ylidene)-1-piperidinecarboxylate; mp. 105.9° C. (comp. 12).

In a similar way there were prepared:

ethyl 4-(8-fluoro-5,6-dihydro-11H-[1,2,4]triazolo[5, 1-b][3]benzazepin-11-ylidene)-1-piperidinecarboxylate; mp. 118.2° C. (comp. 13);

ethyl 4-(5,6-dihydro-7-methyl-11H-[1,2,4]triazolo[5,1-b][31 benzazepin-11-ylidene)-1-piperidinecarboxylate (comp. 14); mp. 163.0° C.; and ethyl 4-(9-chloro-5,6-dihydro-11H-[1,2,4]triazolo[5,1-b][3]benzazepin-11-ylidene)-1-piperidinecarboxylate (comp. 15).

b) A mixture of compound (12) (0.051 mol) in an aqueous hydrobromic acid solution 48% (315 ml) was stirred and heated at 100° C. for 6 hours. The mixture was cooled, poured into ice, basified with ammonia and extracted with dichloromethane. The organic layer was dried (MgSO$_4$), filtered off and evaporated. The residue (10.2 g) was purified by column chromatography over silica gel (eluent: CH$_2$Cl$_2$/CH$_3$OH/NH$_4$OH 93/7/0.2) (15–40 µm). The pure fractions were collected and evaporated, yielding 9.2 g (68%) of product. A sample (2 g) was crystallized from 2-butanone/2,2'-oxybispropane, yielding 1.88 g of 6,11-dihydro-11-(4-piperidinylidene)-5H-[1,2,4]triazolo[5,1-b]benzazepine hemihydrate; mp. 116.2° C. (comp. 16).

In a similar way there were prepared:

8-fluoro-6,11-dihydro-11-(4-piperidinylidene)-5H-l 1,2,4]triazolo[5,1-b]13]benzazepine hemihydrate; mp. 125.3° C. (comp. 17);

9-chloro-6,11-dihydro-11-(4-piperidinylidene)-5H-[1,2,4]triazolo[5,1-b][3]benzazepine ethanedioate (1:1); mp. 217.5° C. (comp. 18); and 6,11-dihydro-7-methyl-11-(4-piperidinylidene)-5H-[1,2,4]triazolo[5,1-b][3]benzazepine hemihydrate; mp. 144.0° C. (comp. 19).

EXAMPLE 10

A mixture of compound (16) (0.00751 mol), 1-(2-bromoethyl)-4-methoxybenzene (0.0113 mol), potassium iodide (0.125 g) and potassium carbonate (2.1 g) in 4-methyl-2-pentanone (50 ml) was stirred and refluxed overnight. The mixture was cooled and evaporated. The residue was taken up in dichloromethane. The organic layer was washed with water, dried (MgSO$_4$), filtered off and evaporated. The residue (4.5 g) was purified by column chromatography over silica gel (eluent: CH$_2$Cl$_2$/CH$_3$OH/NH$_4$OH 99.5/1.5/0.2 to 98/2/0.2) (15 µm). The pure fractions were collected and evaporated. The residue (2.5 g) was recrystallized from 2-propanone/2,2'-oxybispropane, yielding 1.94 g (88%) of 6,11-dihydro-11-[1-[2-(4-methoxyphenyl)ethyl]-4-piperidinylidene]-5H-[1,2,4]triazolo[5,1-b][3]benzazepine; mp 129.3° C. (comp. 20).

In a similar way there were prepared:

8-fluoro-6,11-dihydro-11-[1-[2-(4-methoxyphenyl)ethyl]-4-piperidinylidene]-5H-[1,2,4]triazolo[5,1-b][3]benzazepine; mp. 128.2° C. (comp. 21);

6-[2-[4-(8-fluoro-5,6-dihydro-11H-[1,2,4]triazolo[5,1-b][3]benzazepin-11-ylidene)-1-piperidinyl]ethyl]-7-methyl-5H-thiazolo[3,2-a]pyrimidin-5-one; mp. 196.2° C. (comp. 22);

8-fluoro-6,11-dihydro-11-[1-[2-(2-pyridinyl)ethyl]-4-piperidinylidene]-5H-[1,2,4]-triazolo[5,1-b][3]benzazepine ethanedioate(1:2) hemihydrate; mp. 161.7° C. (comp. 23);

6-[2-[4-(8-fluoro-5,6-dihydro-1 H-[1,2,4]triazolo[5,1-b][3]benzazepin-11-ylidene)-1-piperidinyl]ethyl]-2,3-dihydro-7-methyl-5H-thiazolo[3,2-a]pyrimidin-5-one monohydrate; mp. 129.7° C. (comp. 24);

3-[2- [4-(8-fluoro-5,6-dihydro-11H-[1,2,4]triazolo[5,1-b][3]benzazepin-11-ylidene)-1-piperidinyl]ethyl]-2-methyl-4H-pyrido[1,2-a]pyrimidin-4-one; mp. 176.4° C. (comp. 25);

1-[1-[4-(8-fluoro-5,6-dihydro-11H-[1,2,4]triazolo[5,1-b][3]benzazepin-11-ylidene)-1-piperidinyl]propyl]-1,3-dihydro-2H-benzimidazol-2-one hemihydrate; mp. 131.8° C. (comp. 26);

1-ethyl-4-[2-[4-(8-fluoro-5,6-dihydro-11H-[1,2,4]triazolo[5,1-b][3]benzazepin-11-ylidene)-1-piperidinyl]ethyl]-1,4-dihydro-5H-tetrazol-5-one ethanedioate(2:5); mp. 190.0° C. (comp. 27);

11-[1-[3-(4-fluorophenoxy)propyl]-4-piperidinylidene]-6,11-dihydro-5H-[1,2,4]-triazolo[5,1-b][3]benzazepine ethanedioate(1:1); mp. 185.5° C. (comp. 28);

(E)-8-fluoro-6,11-dihydro-11-[1-(3-phenyl-2-propenyl)-4-piperidinylidene]-5H-[1,2,4]triazolo[5,1-b][3]benzazepine ethanedioate(1:1); mp. 212.9° C. (comp. 29);

3-[2-[4-(5,6-dihydro-11H-[1,2,4]triazolo[5,1-b][3]benzazepin-11-ylidene)-1-piperidin-yl]ethyl]-2-oxazolidinone ethanedioate(l: 1) hemihydrate; mp. 160.2° C. (comp. 30);

11-[1-(2-ethoxyethyl)-4-piperidinylidene]-6,11-dihydro-5H-[1,2,4]triazolo[5,1-b]-[3]benzazepine; mp. 99.0° C. (comp. 31); and 4-(5,6-dihydro-11H-[1,2,4]triazolo[5,1-b][3]benzazepin-11-ylidene)-1-piperidineacetonitrile; mp. 161.5° C. (comp. 32).

EXAMPLE 11

Boron tribromide (28 ml) was added dropwise at 0° C. to a solution of compound (21) (0.00471 mol) in dichloromethane (50 ml) and the mixture was stirred at room temperature for 24 hours. The mixture was poured into ice, basified with potassium carbonate and extracted with dichloromethane. The organic layer was dried (MgSO$_4$), filtered off and evaporated. The residue (1.8 g) was purified by column chromatography over silica gel (eluent: CH$_2$Cl$_2$/CH$_3$OH/NH$_4$OH 96/4/0.5) (15–40 μm). The pure fractions were collected and evaporated. The residue (0.61 g) was converted into the ethanedioic acid salt (1:1) in 2-propanone, yielding 0.57 g (32%) of 4-[2-[4-(8-fluoro-5,6-dihydro-11H-[1,2,4]triazolo[5,1-b][3]benzazepin-11-ylidene)-1-piperidinyl]ethyl]-phenol ethanedioate (1:1) hemihydrate; mp. 181.2° C. (comp. 33).

EXAMPLE 12

A mixture of compound (32) (0.0245 mol) in methanol saturated with ammonia (200 ml) was hydrogenated for 12 hours in a Parr apparatus (room temperature; pressure: 3 bars) with Raney nickel (7.5 g) as a catalyst. After uptake of hydrogen (2 eq.), the flask was flushed with nitrogen, the catalyst was filtered off and the filtrate was evaporated, yielding 7.3 g (96%) of 4-(5,6-dihydro-11H-[1,2,4]triazolo[5,1-b][3]benzazepin-11-ylidene)-1-piperidineethanamine (used without further purification in next reaction step) (comp. 34). The product was purified by column chromatography over silica gel (eluent: CH$_2$Cl$_2$/CH$_3$OH/NH$_4$OH 90/10/1) (15–40 μm). The pure fractions were collected and evaporated. The residue (2.7 g) was converted into the (E)-2-butenedioic acid salt (1:2) and recrystallized from methanol (abs.), yielding 1.53 g of 4-(5,6-dihydro-11H-[1,2,4]triazolo[5,1-b][3]benzazepin-11-ylidene)-1-piperidineethanamine (E)-2-butenedioate (1:2) hydrate (2:5); mp. 184.3° C. (comp. 35).

EXAMPLE 13

A solution of 1,1'-carbonylbis-1H-imidazole (0.028 mol) in tetrahydrofuran was added dropwise at room temperature to a solution of compound (34) (0.00937 mol) in tetrahydrofuran and the mixture was stirred at room temperature for 1 hour. A solution of methanamine (40%) (1.5 g) in water was added dropwise and the mixture was stirred at room temperature for 12 hours. The mixture was evaporated and the residue was taken up in dichloromethane. The organic layer was washed with saturated aqueous sodium chloride, dried (MgSO$_4$), filtered off and evaporated. The residue (3.6 g) was purified by column chromatography over silica gel (eluent: CH$_2$Cl$_2$/CH$_3$OH/NH$_4$OH 92/8/0.5) (15–40 μm). The pure fractions were collected and evaporated, yielding 2.4 g of product. A sample (1.95 g) was converted into the (E)-2-butenedioic acid salt (1:1) in ethanol, yielding 1.95 g (56.8%) of N-[2-[4-(5,6-dihydro-11H-[1,2,4]triazolo[5,1-b]-[3]benzazepin-11-ylidene)-1-piperidinyl]ethyl]-N'-methylurea (E)-2-butenedioate(1:1); mp. 196.3° C. (comp. 36).

EXAMPLE 14

A mixture of 3-furancarboxylic acid (0.00741 mol), 2-chloro-1-methylpyridium iodide (0.00744 mol) and N,N-diethylethanamine (1.5 g) in dichloromethane was stirred at room temperature for 1 hour. A solution of compound (34) (0.00743 mol) in dichloromethane was added dropwise and the mixture was stirred at room temperature for 48 hours. The mixture was poured into potassium carbonate 5%, extracted with dichloromethane and washed with water. The organic layer was dried (MgSO$_4$), filtered off and evaporated. The residue was purified by column chromatography over silica gel (eluent: CH$_2$Cl$_2$/CH$_3$OH/NH$_4$OH 95/5/0.5) (15–40 μm). The pure fractions were collected and evaporated. The residue (1.9 g) was recrystallized from 2-butanone, yielding 1.15 g (38%) of N-[2-[4-(5,6-dihydro-11H-[1,2,4]triazolo[5,1-b][3]benzazepin-11-ylidene)-1-piperidinyl]ethyl]-3-furancarboxamide hemihydrate; mp. 167.2° C. (comp. 37).

EXAMPLE 15

A mixture of compound (34) (0.00969 mol), 2-chloropyrimidine (0.0116 mol) and potassium carbonate (0.0194 mol) in N,N-dimethylformamide (100 ml) was stirred and refluxed for 12 hours. The reaction mixture was cooled to room temperature and the solvent was evaporated. The residue was stirred in water and this mixture was extracted with dichloromethane. The separated organic layer was washed with water, dried (MgSO$_4$), filtered and the solvent was evaporated. The residue (3.1 g) was purified by column chromatography over silica gel (300 g; 15–40 μm; eluent: CH$_2$Cl$_2$/CH$_3$OH/NH$_4$OH 95/5/0.2). The pure fractions were collected and the solvent was evaporated. The residue (1.95 g) was recrystallized from 2-butanone. The precipitate was filtered off and dried, yielding 1.1 g (29%) of N-[2-[4-(5,6-dihydro-11H-[1,2,4]triazolo[5,1-b][3]-benzazepin-11-ylidene)-1-piperidinyl]ethyl]-2-pyrimidinamine; mp. 161.5° C. (comp. 38).

EXAMPLE 16 a) Methyl 2-propenoate (0.0176 mol) was added dropwise to a mixture of compound (17) (0.0088 mol) in methanol (30 ml) and the mixture was stirred and refluxed for 12 hours.

The mixture was evaporated till dryness. The residue was purified by column chromatography over silica gel (eluent: $CH_2Cl_2/CH_3OH/NH_4OH$ 97/3/0.1). The pure fractions were collected as an oil, yielding 2.8 g (86%) of product. The product was converted into the (E)-2-butenedioic acid salt (1:1) in ethanol, yielding 2.7 g (61%) of methyl 4-(8-fluoro-5,6-dihydro-11H-[1,2,4]triazolo[5,1-b][3]benzazepin-11-ylidene)-1-piperidinepropanoate (E)-2-butenedioate (1:1) monohydrate; mp. 170.6° C. (comp. 39).

In a similar way there was prepared:

methyl 4-(5,6-dihydro-11H-[1,2,4]triazolo[5,1-b][3]benzazepin-11-ylidene)-1-piperidinepropanoate ethanedioate(2:3). hemihydrate; mp. 144.4° C. (comp. 40).

b) A mixture of compound (39) (0.0081 mol) and potassium hydroxide (0.45 g) in water (10 ml) and tetrahydrofuran (80 ml) was stirred at room temperature overnight. The mixture was evaporated and the residue was extracted with dichloromethane. The aqueous layer was evaporated, the residue was neutralized with HCl 1N and evaporated till dryness. The product (2.05 g) was recrystallized from water, yielding 1.2 g (38%) of 4-(8-fluoro-5,6-dihydro-11H-[1,2,4]triazolo[5,1-b][3]benzazepin-11-ylidene)-1-piperidinepropanoic acid dihydrate; mp. 120.1° C. (comp. 41).

EXAMPLE 17

At 0° C., oxirane (2 eq.) was allowed to bubble through methanol. This mixture was added dropwise to a solution of compound (16) (0.0113 mol) in methanol, stirred at room temperature. The reaction mixture was stirred for 24 hours at room temperature. The solvent was evaporated. The residue was taken up in dichloromethane, washed with water, dried ($MgSO_4$), filtered and the solvent was evaporated. The residue was purified by column chromatography over silica gel (260 g; 15–40 µm; eluent: $CH_2Cl_2/CH_3OH/NH_4OH$ 95/5/0.3). The pure factions were collected and the solvent was evaporated. The residue (2.3 g) was recrystallized from 2-butanone. The precipitate was filtered off and dried, yielding 1.62 g (46%) 4-(5,6-dihydro-11H-[1,2,4]triazolo-[5,1-b][3]benzazepin-11-ylidene)-1-piperidineethanol; mp. 153.7° C. (comp. 42).

EXAMPLE 18

A mixture of compound (17) (0.01 mol), (±)-[(4-fluorophenoxy)methyl]oxirane (0.02 mol) and potassium carbonate (1.38 g) in acetonitrile (150 ml) was stirred and refluxed for 20 hours. The mixture was filtered off and the filtrate was evaporated. The oily residue was taken up in dichloromethane. The organic layer was washed with water, dried ($MgSO_4$), filtered off and evaporated till dryness. The residue was purified by column chromatography over silica gel (eluent: $CH_2Cl_2/CH_3OH/NH_4OH$ 97/3/0.1). The pure fractions were collected and evaporated, yielding 2.6 g (57%). The product was crystallized from 1,1'-oxybisethane, yielding 1.7 g (38%) of (±)-4-(8-fluoro-5,6-dihydro-11H-[1,2,4]triazolo[5,1-b][3]benzazepin-11-ylidene)-α-[(4-fluorophenoxy)-methyl]-1-piperidineethanol; mp. 134.4° C. (comp. 43).

EXAMPLE 19

Compound (5) (0.00767 mol) in ethanol (200 ml) was hydrogenated with palladium on activated carbon (2.2 g) as a catalyst at 50° C. over a 5 hours period under a 3 bar pressure in a Parr apparatus. After uptake of hydrogen (1 eq.), the catalyst was filtered through celite and the filtrate was evaporated. The residue (2.1 g) was purified by column chromatography over silica gel (eluent: $CH_2Cl_2/CH_3OH/NH_4OH$ 94/6/0.5 to 90/10/0.5) (15–40 µm). The pure fractions were collected and evaporated. The residue was crystallized from 2,2'-oxybispropane, yielding 1.22 g (83%) of (±)-6,11-dihydro-11-(1-methyl-4-piperidinyl)-5H-[1,2,4]triazolo[5,1-b][3]benzazepine; mp. 133.8° C. (comp. 44).

EXAMPLE 20

A mixture of compound (8) (0.0327 mol) and sodium acetate (few g) in formaldehyde (540 ml) and acetic acid (80 ml) was stirred at 130° C. overnight. The mixture was cooled, poured into ice, basified with ammonia and extracted with dichloromethane. The organic layer was washed with water, dried ($MgSO_4$), filtered off and evaporated till dryness. The residue was taken up in HCl 3N and washed with ethyl acetate. The aqueous layer was basified with sodium hydroxide 3N and extracted with ethyl acetate. The organic layer was dried ($MgSO_4$), filtered off and evaporated till dryness. The residue was purified by column chromatography over silica gel (eluent: $CH_2Cl_2/CH_3OH/NH_4OH$ 90/10/1). The pure fractions were collected and evaporated, yielding 7.71 g (76%). A sample (2 g) was recrystallized from 2-propanol, yielding 1.2 g of 6,11-dihydro-11-(1-methyl-4-piperidinylidene)-5H-1,2,4-triazolo[3,4-b][3]benzazepine-3-methanol hemihydrate; mp. 250.1° C. (comp. 45).

C. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I) or a compound of formula (VII), a pharmaceutically acceptable acid addition salt or a stereochemically isomeric form thereof.

EXAMPLE 21

Oral Drops 500 g of the A.I. is dissolved in 0.5 l of 2-hydroxypropanoic acid and 1.5 l of the polyethylene glycol at 60–80° C. After cooling to 30–40° C. there are added 35 g of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 22

Oral Solutions 9 g of methyl 4-hydroxybenzoate and 1 g of propyl 4-hydroxybenzoate are dissolved in 4 ;l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 23

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 24

Film-coated Tablets thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

EXAMPLE 25

Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 26

Suppositories 3 g A.I. is dissolved in a solution of 3 g 2,3-dihydroxybutanedioic acid in 25 ml polyethylene glycol 400. 12 g surfactant (SPAN®) and triglycerides (Witepsol 555®) q.s. ad 300 g are molten together. The latter mixture is mixed well with the former solution. The thus obtained mixture is poured into moulds at a temperature of 37–38° C. to form 100 suppositories each containing 30 mg of the A.I.

We claim:

1. A compound having the formula

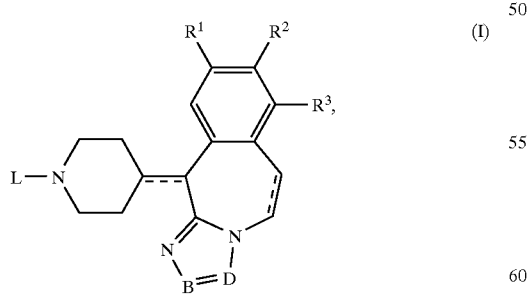

a pharmaceutically acceptable addition salt or a stereochemically isomeric form thereof, wherein each of the dotted lines independently represents an optional bond, $R^1$ represents hydrogen, halo, $C_{1-4}$alkyl, hydroxy or $C_{1-4}$alkyloxy;

$R^2$ represents hydrogen, halo, $C_{1-4}$alkyl, hydroxy or $C_{1-4}$alkyloxy;

$R^3$ represents hydrogen, $C_{1-4}$alkyl or halo;

—B═D— is a bivalent radical of formula

—C($R^4$)═N—  (a-1);

or

—N═C($R^5$)—  (a-2);

$R^4$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^5$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl, hydroxycarbonyl, phenyl or pyridinyl;

L represents hydrogen; $C_{1-6}$alkyl; $C_{1-6}$alkyl substituted with one substituent selected from the group consisting of hydroxy, $C_{1-4}$alkyloxy, hydroxycarbonyl, $C_{1-4}$alkyloxycarbonyl, $C_{1-4}$alkyloxycarbonyl$C_{1-4}$alkyloxy, hydroxycarbonyl-$C_{1-4}$alkyloxy, $C_{1-4}$alkylaminocarbonylamino, $C_{1-4}$alkylaminothiocarbonylamino, aryl and aryloxy; $C_{1-6}$alkyl substituted with both hydroxy and aryloxy; $C_{3-6}$alkenyl; $C_{3-6}$alkenyl substituted with aryl;

wherein each aryl is phenyl or phenyl substituted with halo, cyano, hydroxy, $C_{1-4}$alkyl, $C_{1-4}$alkyloxy or aminocarbonyl; or, L represents a radical of formula —Alk—Y—Het$^1$  (b-1), —Alk—NH—CO—Het$^2$  (b-2) or —Alk—Het$^3$  (b-3); wherein Alk represents $C_{1-4}$alkanediyl;

Y represents O, S or NH;

Het$^1$, Het$^2$ and Het$^3$ each represent furanyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and Het$^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

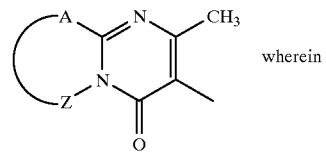

wherein

—A—Z— represents —S—CH═CH—, —S—CH$_2$—CH$_2$—, —S—CH$_2$—CH$_2$—CH$_2$—, —CH═CH—CH═CH— or —CH$_2$—CH$_2$—CH$_2$—CH$_2$—.

2. A compound according to claim 1 wherein —B═D— is a bivalent radical of formula —C(R⁴)═N— (a-1).

3. A compound according to claim 2 wherein L represents $C_{1-4}$alkyl or a radical of formula Alk-Het³ (b-3).

4. A compound according to claim 1 wherein said compound is 6,11-dihydro-11-(1-methyl-4-piperidinylidene)-5H-1,2,4-triazolo[5,1-b][3]benzazepine, a stereochemically isomeric form thereof or an acid addition salt thereof.

5. A pharmaceutical composition comprising as an active ingredient a therapeutically effective amount of a compound as defined in claim 1 and a pharmaceutically acceptable carrier.

6. A compound having the formula

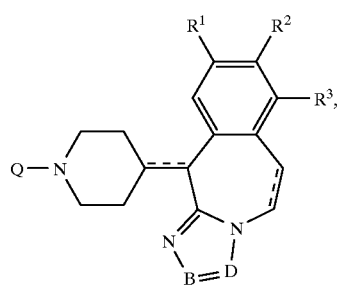

(VII)

an addition salt thereof or a stereochemically isomeric form thereof, wherein each of the dotted lines independently represents an optional bond, $R^1$ represents hydrogen, halo, $C_{1-4}$alkyl, hydroxy, or $C_{1-4}$alkyloxy;

$R^2$ represents hydrogen, halo, $C_{1-4}$alkyl, hydroxy or $C_{1-4}$alkyloxy;

$R^3$ represents hydrogen, $C_{1-4}$alkyl or halo;

—B═D— is a bivalent radical of formula

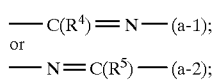

$R^4$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^5$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl, hydroxycarbonyl, phenyl or pyridinyl;

Q represents $C_{1-6}$alkyloxycarbonyl, $C_{1-4}$alkylcarbonyl or $C_{1-6}$alkyl substituted with halo, cyano, amino or methylsulfonyloxy.

7. A compound having the formula

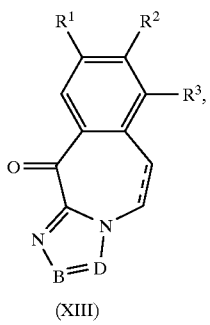

(XIII)

or

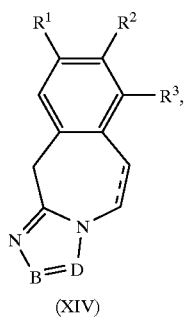

(XIV)

an addition salt form thereof or a stereochemically isomeric form thereof, wherein the dotted line, $R^1$, $R^2$, $R^3$ and —B═D— are as defined in claim 1, provided that 11H-1,2,4-triazolo[3,4-b][3]benzazepine is excluded.

8. A method for the treatment of allergic disease which comprises administering to a warm blooded animal suffering from allergic disease a therapeutically effective amount of a compound as defined in claim 1.

9. A method for the treatment of allergic disease which comprises administering to a warm blooded animal suffering from allergic disease a therapeutically effective amount of a compound as defined in claim 2.

10. A method for the treatment of allergic disease which comprises administering to a warm blooded animal suffering from allergic disease a therapeutically effective amount of a compound as defined in claim 3.

11. A method for the treatment of allergic disease which comprises administering to a warm blooded animal suffering from allergic disease a therapeutically effective amount of a compound as defined in claim 4.

12. A pharmaceutical composition comprising as an active ingredient a therapeutically effective amount of a compound as defined in claim 2 and a pharmaceutically acceptable carrier.

13. A pharmaceutical composition comprising as an active ingredient a therapeutically effective amount of a compound as defined in claim 3 and a pharmaceutically acceptable carrier.

14. A pharmaceutical composition comprising as an active ingredient a therapeutically effective amount of a compound as defined in claim 4 and a pharmaceutically acceptable carrier.

* * * * *